(12) United States Patent
Pecherer (10) Patent No.: US 9,968,248 B2
(45) Date of Patent: May 15, 2018

(54) LARYNGOSCOPE AND HANDLE THEREOF

(71) Applicant: Evgeny Pecherer, Netanya (IL)

(72) Inventor: Evgeny Pecherer, Netanya (IL)

( * ) Notice: Subject to any disclaimer, the term of this patent is extended or adjusted under 35 U.S.C. 154(b) by 275 days.

(21) Appl. No.: 14/917,580

(22) PCT Filed: Sep. 10, 2014

(86) PCT No.: PCT/IB2014/064396
§ 371 (c)(1),
(2) Date: Mar. 9, 2016

(87) PCT Pub. No.: WO2015/036938
PCT Pub. Date: Mar. 19, 2015

(65) Prior Publication Data
US 2016/0220106 A1    Aug. 4, 2016

Related U.S. Application Data

(60) Provisional application No. 61/876,779, filed on Sep. 12, 2013.

(51) Int. Cl.
| | | |
|---|---|---|
| *A61B 1/267* | (2006.01) | |
| *A61B 1/06* | (2006.01) | |
| *A61B 1/00* | (2006.01) | |
| *A61B 1/04* | (2006.01) | |

(52) U.S. Cl.
CPC .......... *A61B 1/267* (2013.01); *A61B 1/00032* (2013.01); *A61B 1/00066* (2013.01); *A61B 1/00071* (2013.01); *A61B 1/04* (2013.01); *A61B 1/0669* (2013.01); *A61B 1/0684* (2013.01)

(58) Field of Classification Search
CPC .............. A61B 1/0669; A61B 1/00066; A61B 1/00032; A61B 1/267
See application file for complete search history.

(56) References Cited

U.S. PATENT DOCUMENTS

| | | | |
|---|---|---|---|
| 3,985,131 A | 10/1976 | Buck et al. | |
| 4,037,588 A * | 7/1977 | Heckele | A61B 1/267 600/191 |
| 4,924,862 A | 5/1990 | Levinson | |
| 5,060,633 A | 10/1991 | Gibson | |
| 5,259,377 A | 11/1993 | Schroeder | |
| 5,551,946 A | 9/1996 | Bullard | |
| 5,664,560 A | 9/1997 | Merrick et al. | |

(Continued)

FOREIGN PATENT DOCUMENTS

| | | |
|---|---|---|
| JP | 05329095 A | 12/1993 |
| WO | 2010065566 A2 | 6/2010 |
| WO | 2011119521 A1 | 9/2011 |

*Primary Examiner* — Christian Sevilla
(74) *Attorney, Agent, or Firm* — Alphapatent Associates, LTD; Daniel J. Swirsky (57) ABSTRACT

A laryngoscope handle is provided. The laryngoscope handle comprises a lower grip and an upper functional portion comprising a blade-retention portion formed with a slot extending in a longitudinal direction parallel to a viewing axis, and being configured for slidingly receiving therewithin a laryngoscope blade, and a light source disposed above the slot and being directed substantially parallel to the viewing axis. A majority of the area above the slot and surrounding the light source is substantially free of visual obstructions along the viewing axis.

17 Claims, 7 Drawing Sheets

(56) References Cited

U.S. PATENT DOCUMENTS

| | | | |
|---|---|---|---|
| 5,800,344 A * | 9/1998 | Wood, Sr. | A61B 1/267 600/185 |
| 6,004,263 A * | 12/1999 | Nakaichi | A61B 1/00165 600/120 |
| 6,217,514 B1 | 4/2001 | Gruen et al. | |
| 6,634,356 B1 | 10/2003 | O'Dea et al. | |
| 6,719,688 B2 | 4/2004 | Pecherer et al. | |
| 2003/0092967 A1 | 5/2003 | Fourie et al. | |
| 2007/0125374 A1 | 6/2007 | Smith et al. | |
| 2007/0161863 A1 * | 7/2007 | Bentt | A61B 1/267 600/187 |
| 2008/0146878 A1 | 6/2008 | Frost | |
| 2008/0242941 A1 | 10/2008 | Kim et al. | |
| 2009/0050146 A1 | 2/2009 | Smith | |
| 2009/0099421 A1 * | 4/2009 | Shalman | A61B 1/00103 600/197 |
| 2011/0180072 A1 * | 7/2011 | Morejon | A61M 16/04 128/207.14 |
| 2012/0330103 A1 * | 12/2012 | Tenger | A61B 1/043 600/188 |
| 2013/0104896 A1 | 5/2013 | Kimm et al. | |

\* cited by examiner

LARYNGOSCOPE AND HANDLE THEREOF

CROSS-REFERENCE TO RELATED APPLICATIONS

This application is a U.S. National Phase Application under 35 U.S.C. 371 of International Application No. PCT/IB2014/064396, which has an international filing date of Sep. 10, 2014, and which claims priority and benefit from U.S. Provisional Patent Application Ser. No. 61/876,779, filed Sep. 12, 2013, the contents and disclosure of which are incorporated herein by reference in their entirety.

FIELD OF THE INVENTION

The present disclosure relates to laryngoscopes. More particularly, it relates to laryngoscope handles, especially those designed for use with infants and neonates.

BACKGROUND OF THE INVENTION

Endotracheal tubes are utilized in a wide variety of medical procedures to provide an unobstructed air passage to a patient's trachea. In order to facilitate insertion of an endotracheal tube into a patient's airway, a laryngoscope may be used.

A laryngoscope typically comprises a blade, along which the endotracheal tube is guided, and a handle, which is manipulated to alter the position of the blade within the patient's airway. In addition, other features, such as lights, etc., may be provided.

US 2003/0092967 discloses a laryngoscope comprising a handle having an axis and carrying a light source of a type having an axis extending in the general direction in which a light beam is emitted thereby is described. The laryngoscope has a removable and replaceable, preferably disposable, blade of translucent material carried by the handle and extending generally transversely relative to the handle axis. The blade has a proximal end and a distal end, and the light source is directed transversely relative to the axis of the handle so as to aim the light beam directly at, and generally at right angles to, a transverse light receiving face formed at the proximal end of the blade. A light focusing "lens" may be interposed between the light source and the transverse light receiving face. The handle is preferably made of molded plastics material and is ergonomically contoured to form a grip which is comfortable to hold; easy for a medical practitioner to position; and which can be effectively gripped.

SUMMARY OF THE INVENTION

According to one aspect of the presently disclosed subject matter, there is provided a laryngoscope handle comprising a lower grip and an upper functional portion, the functional portion comprising:
 a blade-retention portion formed with a slot extending in a longitudinal direction parallel to a viewing axis, and being configured for slidingly receiving therewithin a laryngoscope blade; and
 a light source disposed above the slot and being directed substantially parallel to the viewing axis;
wherein a majority of the area above the slot and surrounding the light source is substantially free of visual obstructions along the viewing axis.

The laryngoscope handle may further comprise a magnifying glass configured to be disposed behind the area. The magnifying glass may be rotationally articulated to one of the grip and the functional portion.

It will be appreciated that herein the specification and claims, the terms "behind" and "in front of", in particular when used with reference to elements aligned along the viewing axis (e.g., the blade-retention portion, the area thereabove, the light source, etc.) are to be understood as referring, respectively, to proximally and distally.

The blade-retention portion may comprise a securing arrangement configured to retain therein the blade.

The slot may be open to a surface of the blade-retention portion, such as an upwardly-facing surface. The slot may comprise a primary channel spaced from the surface, and a secondary channel spanning between the primary channel and the surface. The primary channel may project outwardly from the secondary channel.

The laryngoscope handle may further comprise an arm connecting between the blade-retention portion the light source. One or more electrical connections may be provided, serving the light source, within the arm.

The light source may comprise a light emitting diode constituting a lamp thereof.

The light source comprises a distal lens. The lens may be configured to focus light from the light source to an angle between about 15° and about 20° along the viewing axis.

The grip may be formed with an internal battery compartment configured to electrically connect one or more batteries inserted therein to the light source to provide power thereto.

The grip may comprise a compartment for a coin cell battery. The compartment for a coin cell battery may be formed within a removable cap of the grip.

The area above the slot and to one side of the light source may be substantially free of visual obstructions along the viewing axis.

The area above the slot and surrounding the light source may be substantially free of visual obstructions along the viewing axis.

The light source may comprise a main lamp and an auxiliary lamp.

The laryngoscope handle may further comprise a switch configured to selectively control operation of the main and auxiliary lamps.

The switch may be configured to selectively turn one or both of the main and auxiliary lamps.

The laryngoscope handle may be configured to receive a camera along the viewing axis. The camera may be rotationally articulated thereto. The laryngoscope may comprise the camera.

According to another aspect of the presently disclosed subject matter, there is provided a laryngoscope comprising:
 the laryngoscope handle as described above; and
 a blade configured to be received within the slot.

The blade may be transparent and configured such that when received within the slot, a proximal side thereof is positioned substantially in front of and facing the light source.

BRIEF DESCRIPTION OF THE DRAWINGS

For a better understanding of the embodiments and to show how it may be carried into effect, reference will now be made, purely by way of example, to the accompanying drawings.

With specific reference now to the drawings in detail, it is stressed that the particulars shown are by way of example and for purposes of illustrative discussion of selected embodiments only, and are presented in the cause of providing what is believed to be the most useful and readily understood description of the principles and conceptual aspects. In this regard, no attempt is made to show structural details in more detail than is necessary for a fundamental understanding; the description taken with the drawings making apparent to those skilled in the art how the several selected embodiments may be put into practice. In the accompanying drawings.

DETAILED DESCRIPTION OF EMBODIMENTS

Figure 1A:
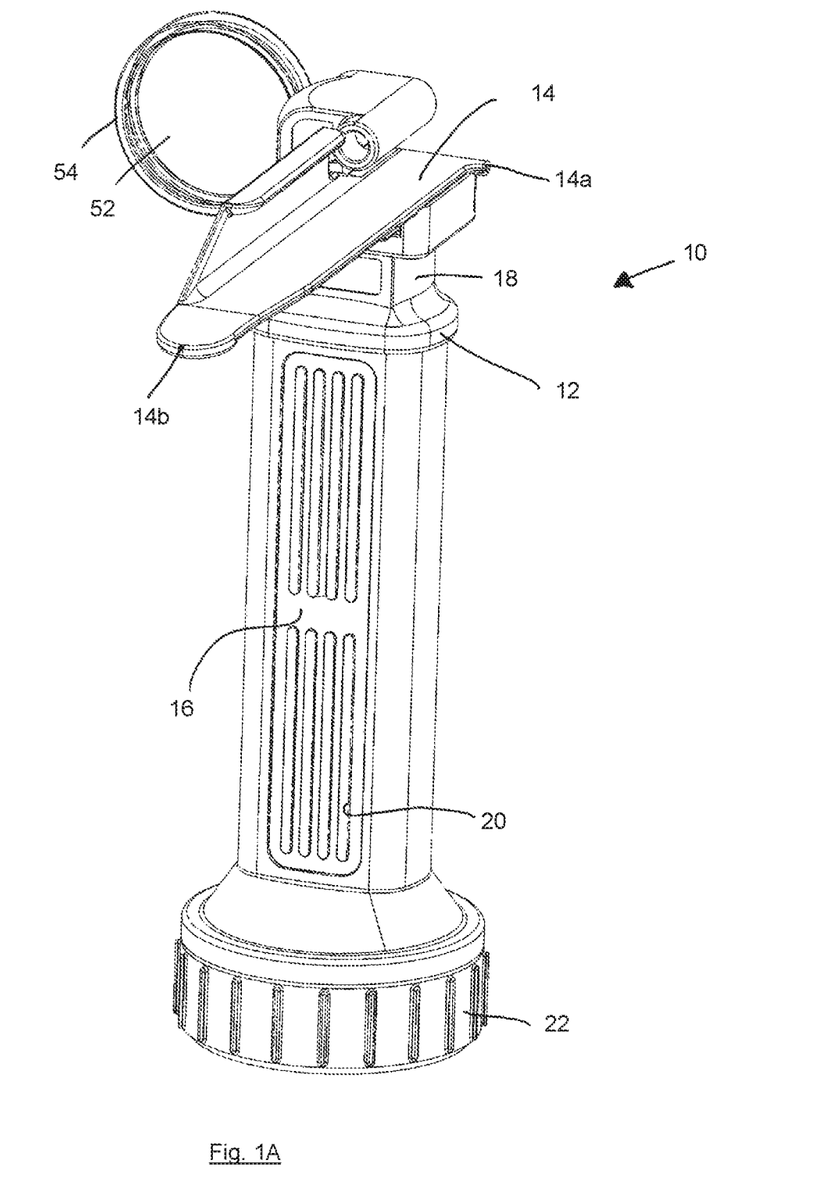
FIGS. 1A and 1B are perspective views of a laryngoscope according to examples of the presently disclosed subject matter.
Figure 1B:
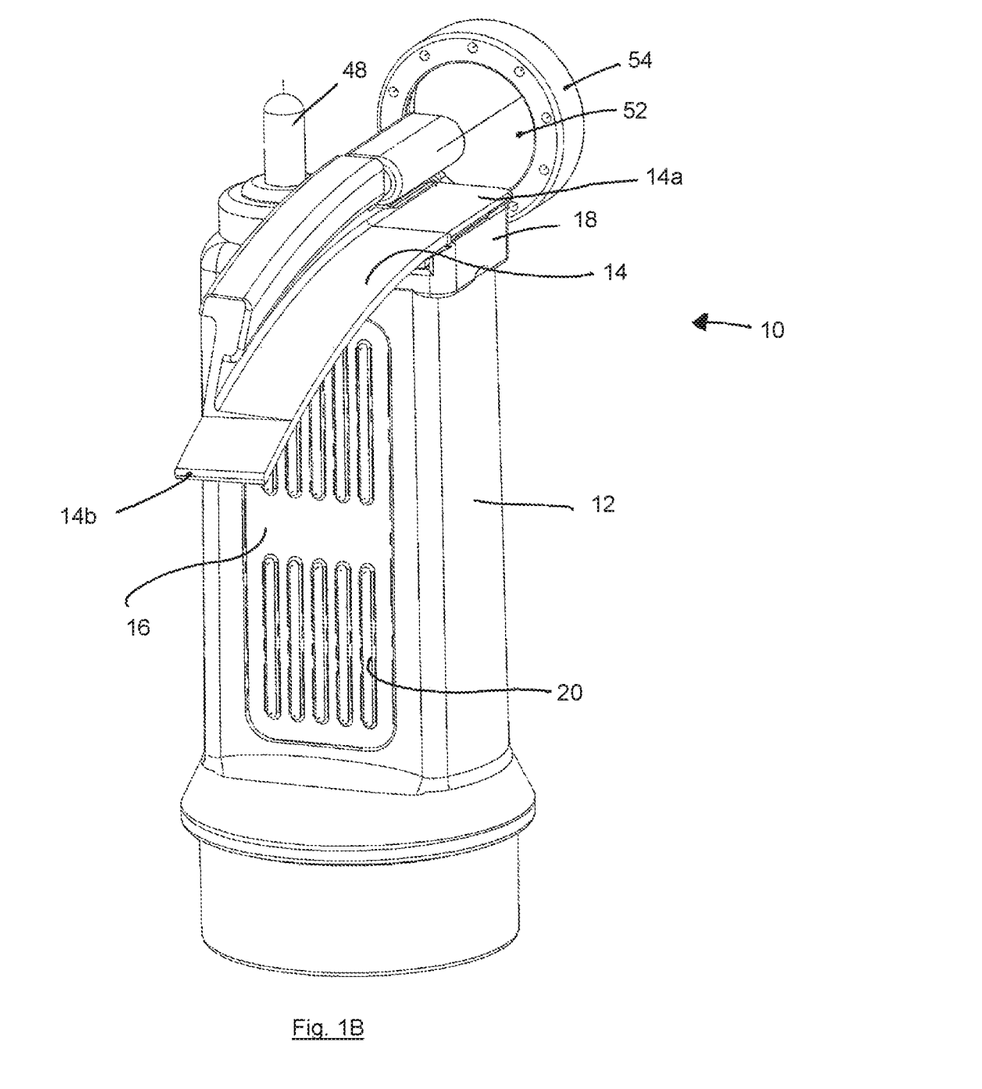

As illustrated in FIGS. 1A and 1B, there is provided a laryngoscope, which is generally indicated at 10, according to the presently disclosed subject matter. The laryngoscope 10 comprises a handle 12 and a blade 14, attached at a proximal end 14a thereof to the handle and which may be removable.

The handle 12 comprises a grip 16, constituting a lower section thereof, and a functional portion 18, constituting an upper portion thereof. It will be appreciated that herein the specification and claims, the terms "upper" and "lower", as well as related terms (such as "up", "down", etc.) are to be understood according to the orientation of the laryngoscope illustrated in FIGS. 1A and 1B, and not according to the orientation than a laryngoscope may be during use.

The grip 16 is constructed so as to facilitate being grasped comfortably and securely by a user performing an intubation procedure with the laryngoscope 10. As such, it may be formed with a plurality of ribs 20, and/or any other suitable feature, such as arcuate indentations (not illustrated) formed to accommodate a user's fingers while grasping the grip 16, etc. IT may be made of any suitable material, such as plastic, an elastomer, etc. In addition, it may be made of more than one material. For example, it may be made primarily of plastic, with some parts thereof such as the ribs 20, being made of an elastomeric material.

Figure 2:
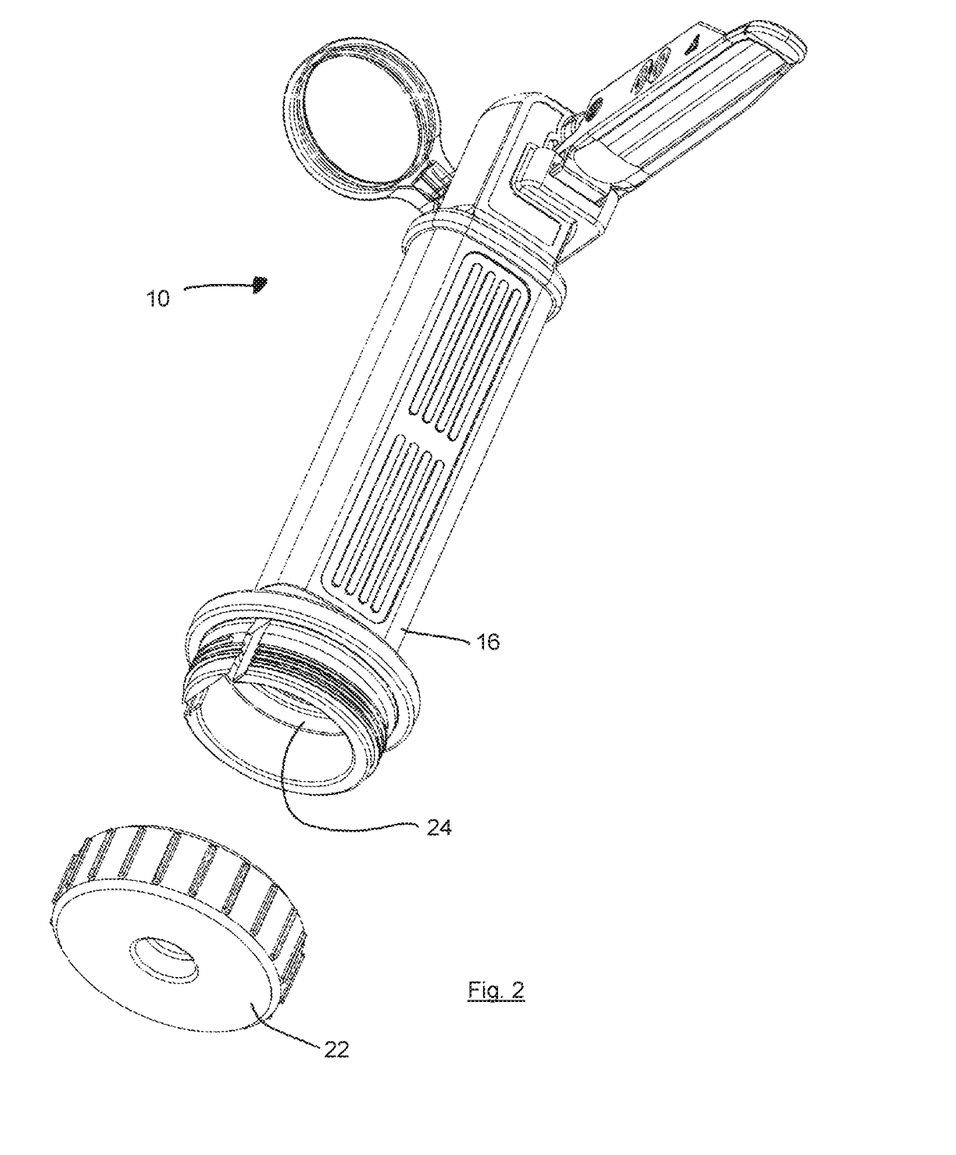
FIG. 2 is an exploded bottom perspective view of the laryngoscope illustrated in FIG. 1A.

As illustrated in FIG. 2, the grip comprises a cap 22 at a bottom end thereof. The cap 22 may be removable, for example screwably, providing access to a hollow interior 24 thereof. The interior 24 may be configured for receiving therein a battery, such as a standard dry cell. Accordingly, besides the interior 24 being shaped to receive and retain the battery, it may comprise necessary conductive elements (not illustrated) to electrically connect it to the functional portion 18 of the handle 12. Thus, the interior 24 may constitute a battery compartment of the laryngoscope 10.

According to some examples, the cap 22 itself is designed so as to receive therein a battery, such as a coin cell battery, with necessary conductive elements provided within the grip 16. According to these examples, the grip 16 need not comprise a hollow interior 24 as described above. However, it may be provided in order to allow for the conductive elements to be easily fitted within the grip 16.

Figure 3:
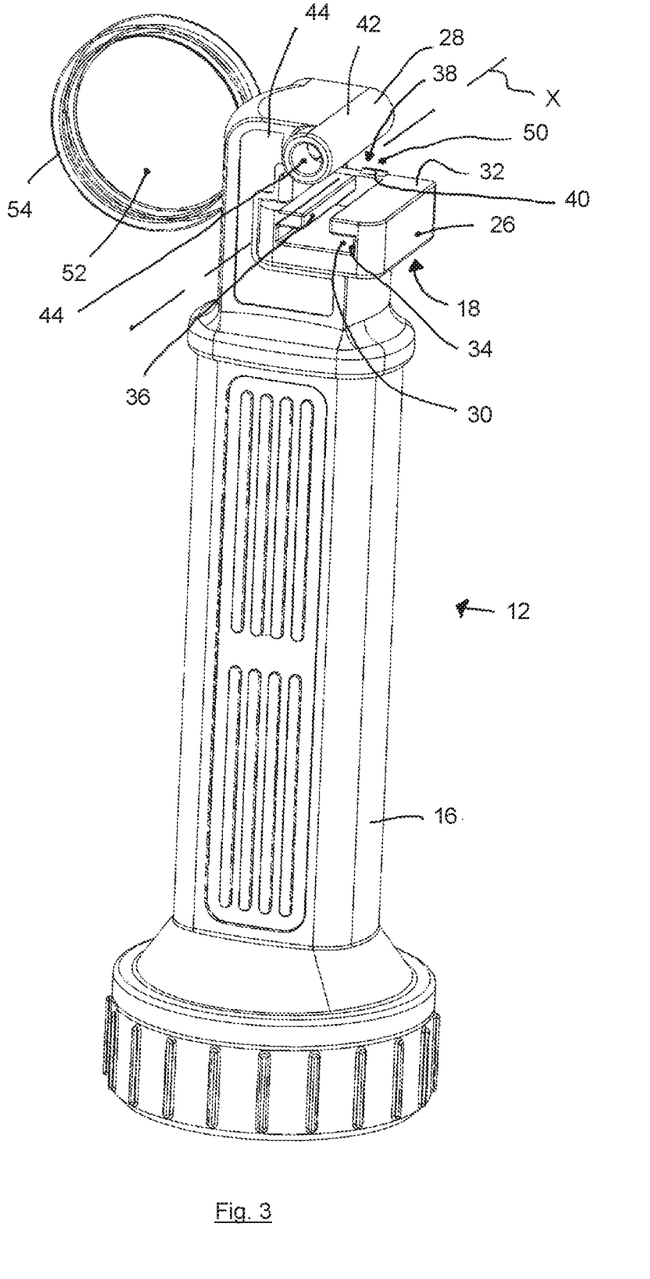
FIG. 3 is a perspective view of a laryngoscope handle of the laryngoscope illustrated in FIG. 1A.

As best seen in FIG. 3, the functional portion 18 of the handle 12 is associated with a viewing axis X, and comprises a blade-retention portion 26, which is configured slidingly receiving therewithin the blade 14, and a light source 28, which is configured to illuminate the blade, in particular a distal end 14b thereof.

As mentioned, the blade-retention portion 26 is configured to slidingly receive the blade 14 therewithin. To facilitate this, it comprises a slot 30 extending parallel to the viewing axis X. The slot 30 may be open to an upper surface 32 of the blade-retention portion 26, and comprise a primary channel 34 spaced from and substantially parallel to the upper surface, and a secondary channel 36 open to the surface and spanning between it and the primary channel, such that the primary channel projects toward both sides of the secondary channel (i.e., an inverted T-shape).

It will be appreciated that although the slot 30 as illustrated herein is open to the upper surface 32 of the blade-retention portion 26, the handle 12 may be designed such that the slot opens to another surface of the blade-retention portion, such as a side surface, or is only open toward a front side thereof.

A securing arrangement 38, configured to retain the blade when inserted therein, may be provided. According to one example, the securing arrangement 38 may comprise a ridge 40 projecting upwardly from the upper surface 32 of the blade-retention portion 26, immediately behind the slot 30, being arranged perpendicularly to the direction of insertion, i.e., to the viewing axis X. A suitable corresponding feature, such as a longitudinal indentation or lip, is formed on the blade 14 to cooperate with the securing arrangement 38.

The securing arrangement 38 may be provided according to any other suitable design, mutatis mutandis. For example, it may comprise a longitudinal indentation or lip, with the corresponding feature on the blade 14 comprising a ridge as described above.

The securing arrangement 38 and corresponding feature on the blade 14 are designed such that the blade may be fully inserted into the slot 30 with a small amount of linear force, and removed by slightly raising the proximal end 14a of the blade. Thus, the blade 14 is retained within the slot 30 during use, but may be easily inserted and removed by a user when necessary.

Reverting to FIG. 3, the light source 28 is disposed so as to illuminate in a direction substantially parallel to the viewing axis X. It comprises a housing 42 extending longitudinally parallel to the viewing axis X, and a lens 44 located at a distal end 42a thereof and provided to focus the light. For example, the lens 44 may be configured to focus the light to within a range of 15°-20°. A lamp (not illustrated) is located within the housing 42, and arranged such that it directs its light toward the lens 44 (e.g., one or more reflective surfaces may be provided for this purpose). The lamp may be any suitable element, such as a light-emitting diode (LED), an incandescent bulb, etc. According to some examples, the lamp and lens may be provided as a single unit (e.g., an LED within an encapsulation dome lens the lens may not be provided.

Power for the light source 28 may be provided by one or more batteries received within the interior 24 of the grip 16, as described above with reference to FIG. 2. Accordingly, an arm 46 connecting between the light source 28 and the blade-retention portion 26 is provided, in which one or more electrical connections (e.g., wires and the like) between the interior 24 of the grip 16 and the light source 28, in particular the lamp thereof. The arm 46 further functions to position the light source 28 over the blade-retention portion 26. In addition, a switch 48 (not illustrated in FIG. 1A), configured to control operation of the light source 28, may be provided.

Reverting to FIGS. 1A and 1B, the position of the light source 28 above the blade-retention portion 26 allows for the light source to be illuminate along a top surface of the blade 12. According to some examples, for example as illustrated in FIG. 1B, the blade may be made of a transparent material, and designed such that when received within the slot, its proximal end 14a is substantially in front of and facing the light source 28. According to this design, the blade 14 constitutes a light guide, transporting light emitted by the light source 28 to the distal end 14b thereof, thereby obviating the need to provide a blade having a dedicated light source.

As can be seen, for example in FIG. 3, the functional portion 18 is designed to provide visual access to a user along the entire length of the blade 14, when looking from its proximal end 14a. Thus, the user is afforded a view parallel to the blade 14 (and the viewing axis X). This may be useful, e.g., for use with small patients such as infants, and particularly neonates. In order to facilitate this, an area 50, or a majority thereof, above the blade-retention portion 26 and/or the slot 30, and surrounding the light source 28 (e.g., to one side, i.e., right or left, thereof), is substantially free of visual obstructions along the viewing axis X.

It will be appreciated that providing a slot 30 which allows for insertion of the blade 14 in a direction which is substantially parallel to the viewing axis X, allows for a design wherein the area 50 above the blade is substantially free of material of the handle, thereby facilitating providing such an area which is free of visual obstructions as described above.

As the design of the functional portion 18 provides visual access along the viewing axis X along the entire length of the blade 14, one or more viewing aids may be provided on the viewing axis. For example, a magnifying glass 52 may be provided, configured to be selectively disposed behind the area 50, i.e., along the viewing axis X.

The magnifying glass 52 may be mounted within a frame 54 which is rotationally articulated to either the grip 16 or the functional portion 18 of the handle 12. This arrangement enables the user to selectively move the magnifying glass into and out of the field of view along the viewing axis X.

Figure 4:
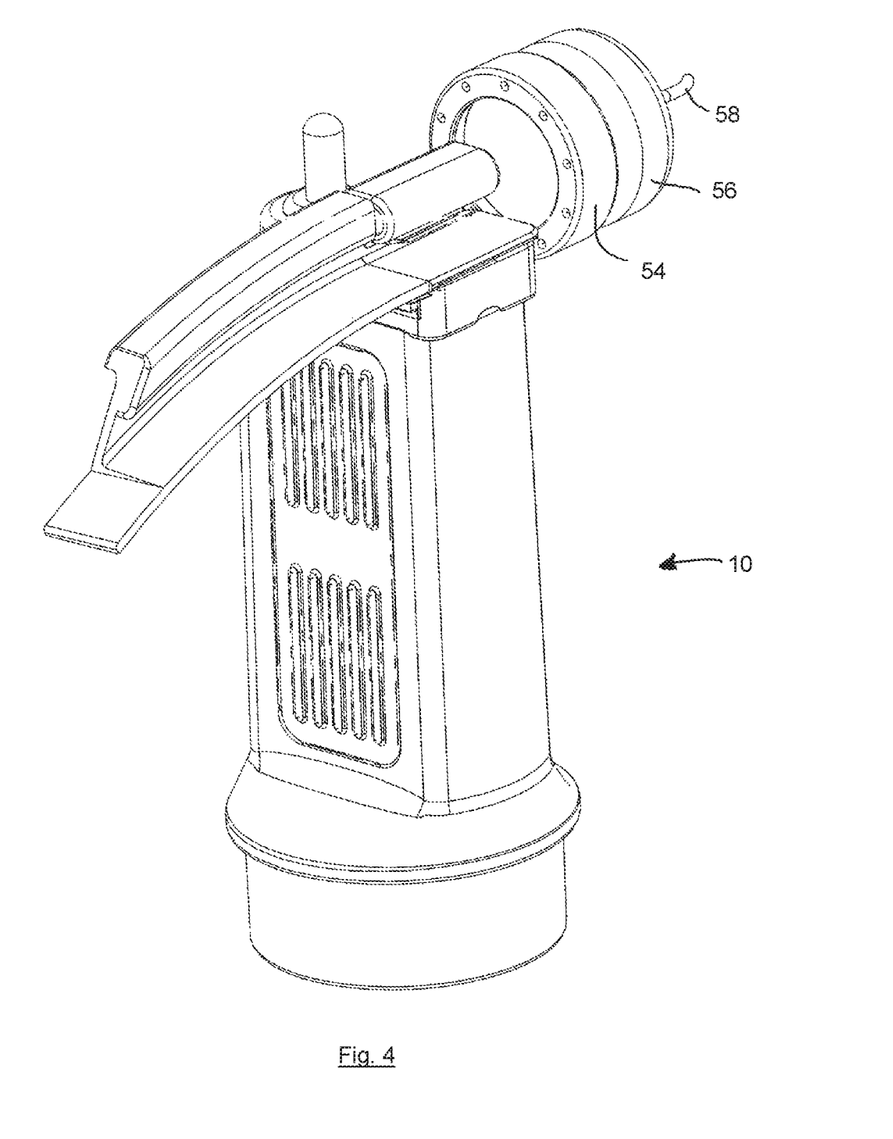
FIG. 4 is a perspective view of the laryngoscope illustrated in FIG. 1B with a camera.

Alternatively or in addition thereto, as illustrated in FIG. 4, a camera 56 may be provided, mounted to the frame 54. The camera 56 may be configured to capture still images and/or video. It may be attached view a wired connection 58 as shown, or wirelessly, according to any suitable protocol, many of which are well known in the art. The camera 56 may be configured to be used in conjunction with the magnifying glass 52, or without it.

Figure 5:
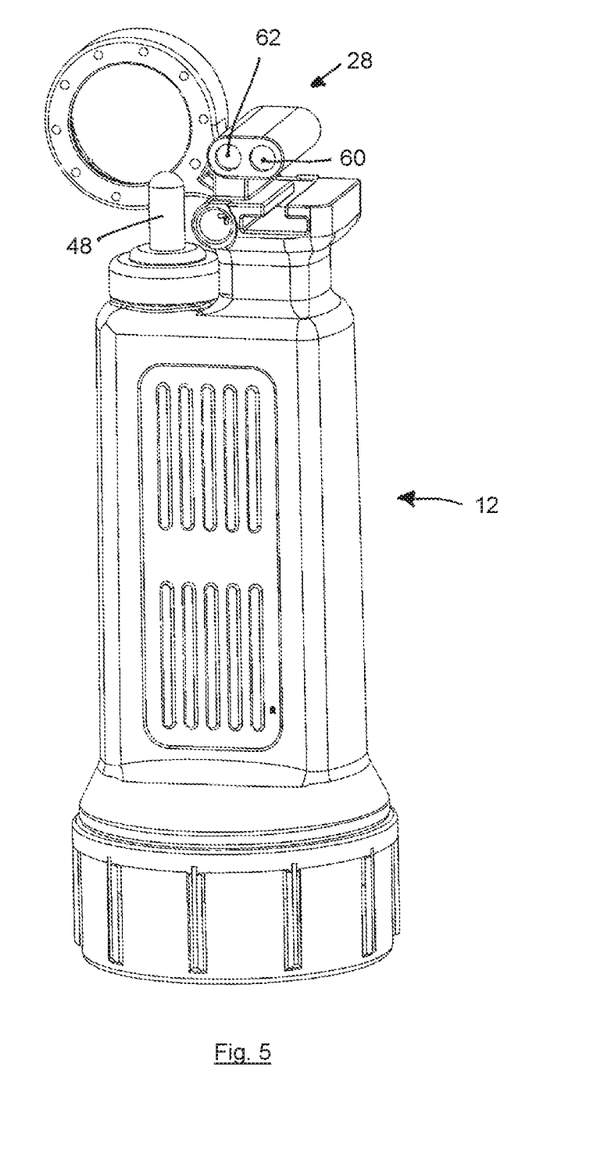
FIG. 5 is a perspective view of a further example of laryngoscope handle according to the presently disclosed subject matter.

As illustrated in FIG. 5, the light source 28 may comprise more than one lamp, e.g., a main lamp (located within the element indicated at 60; for convenience, reference numeral 60 will be used herein the specification and claims to indicate the main lamp, even though it is hidden in FIG. 5) and an auxiliary lamp (located within the element indicated at 62; for convenience, reference numeral 62 will be used herein the specification and claims to indicate the auxiliary lamp, even though it is hidden in FIG. 5). The switch 48 may be configured to selectively turn on the main lamp 60 by itself, or both the main lamp and the auxiliary lamp 62 together. The auxiliary lamp 62 may be useful, for example, to supplement the main lamp 60 to facilitate the handle's 12 use for transillumination (e.g., without the blade 14).

Figure 6:
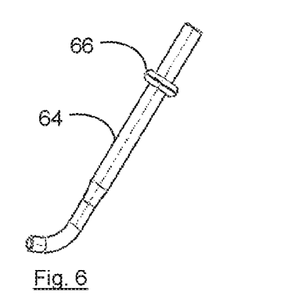
FIG. 6 is an isometric view of intubation guide according to the presently disclosed subject matter.
Figure 7:
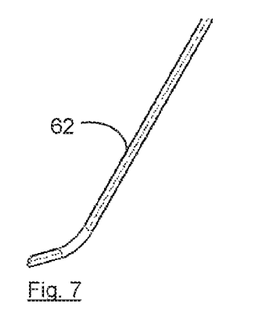
FIG. 7 is an isometric view of a catheter for use with the intubation guide illustrated in FIG. 6.
Figures 8, 9:
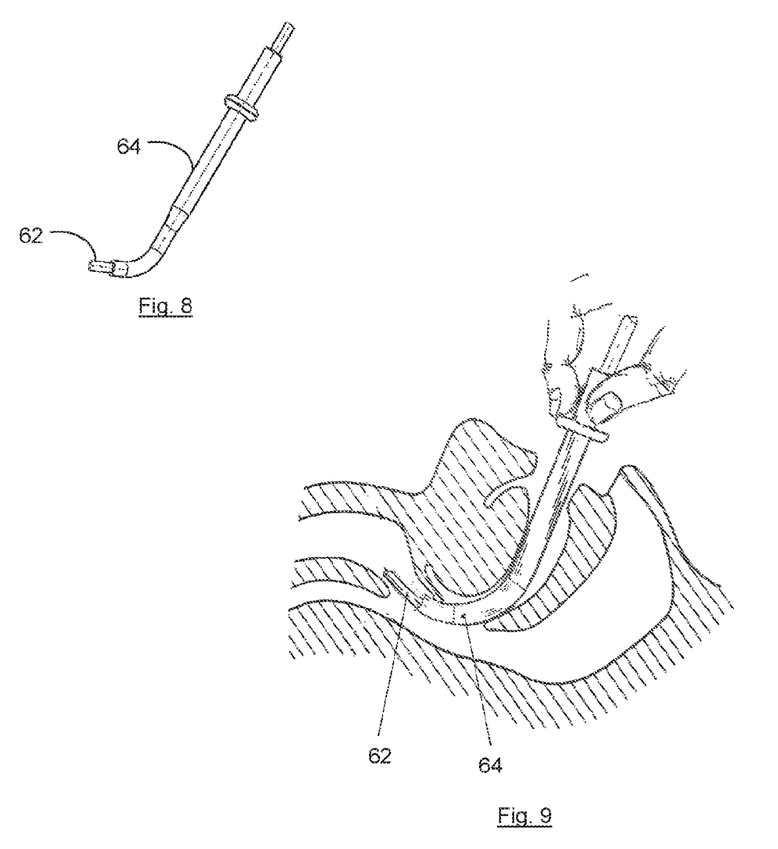
FIG. 8 is an isometric view of the catheter illustrated in FIG. 6 inserted into the intubation guide illustrated in FIG. 7.
FIG. 9 is a pictorial view of the guide with the catheter inserted therein, as illustrated in FIG. 8, in a patient's mouth.

As illustrated in FIGS. 6 through 8, a catheter 62 and a guide 64 may be provided. The catheter 62 may be used for different procedures, for example injection of surfactant materials into the lungs of neonates. The catheter 62 may be made of a flexible plastic material such as PVC, such that it can't be intubated without a guide such as a stylet. The guide 64 may have a "J"-shaped hollow tubular body, made from rigid plastic material, such as polypropylene. The guide 64 may comprise, at an upper part thereof, a bulge 66 providing a user with a place to grip during intubation and fixation of the guide 64 in the mouth, for example after intubation.

Typically, before intubation, the catheter 62 is inserted into the guide 64, as illustrated in FIG. 8, so that its distal end 62a protrudes by about 4-6 mm. This imparts appropriate stiffness and shape for intubation.

After intubation, the guide 64 may be fixed in the patient's mouth with help of adhesive tape, thereby mitigating the risk of spontaneous extubation. The intubation may be conducted with help of the laryngoscope as described above with reference to FIGS. 1 through 5, and/or with any other suitable laryngoscope.

As illustrated in FIG. 9, during intubation, the catheter 62 or an endotracheal tube (not illustrated) is placed into the guide 64. The assembly is then inserted into patient's mouth and moved together with the guide 64 down the patient's throat until reaching the tracheal opening. The laryngoscope blade (not illustrated in FIG. 9) moves the tongue and presses the epiglottis before intubation of the tube, thereby facilitating passage.

Those skilled in the art to which this invention pertains will readily appreciate that numerous changes, variations and modifications can be made without departing from the scope of the invention mutatis mutandis.

Technical and scientific terms used herein should have the same meaning as commonly understood by one of ordinary skill in the art to which the disclosure pertains. Nevertheless, it is expected that during the life of a patent maturing from this application many relevant systems and methods will be developed. Accordingly, the scope of the terms such as computing unit, network, display, memory, server and the like are intended to include all such new technologies a priori.

As used herein the term "about" refers to at least ±10%.

The terms "comprises", "comprising", "includes", "including", "having" and their conjugates mean "including but not limited to" and indicate that the components listed are included, but not generally to the exclusion of other components. Such terms encompass the terms "consisting of" and "consisting essentially of".

The phrase "consisting essentially of" means that the composition or method may include additional ingredients and/or steps, but only if the additional ingredients and/or steps do not materially alter the basic and novel characteristics of the composition or method.

As used herein, the singular form "a", "an" and "the" may include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments or to exclude the incorporation of features from other embodiments.

The word "optionally" is used herein to mean "is provided in some embodiments and not provided in other embodiments". Any particular embodiment of the disclosure may include a plurality of "optional" features unless such features conflict.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween. It should be understood, therefore, that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6 as well as non-integral intermediate values. This applies regardless of the breadth of the range.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination or as suitable in any other described embodiment of the disclosure. Certain features described in the context of various embodiments are not to be considered essential features of those embodiments, unless the embodiment is inoperative without those elements.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the disclosure.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

The invention claimed is:

1. A laryngoscope handle comprising a lower grip and an upper functional portion, said functional portion comprising:

a blade-retention portion formed with a slot extending in a longitudinal direction parallel to a viewing axis, and being configured for slidingly receiving therewithin a laryngoscope blade;

a light source disposed above said slot and being directed substantially parallel to said viewing axis wherein said light source comprises a main lamp and an auxiliary lamp; and a switch configured to selectively control operation of said main and auxiliary lamps;

wherein a majority of the area above said slot and surrounding said light source is substantially free of visual obstructions along said viewing axis; and wherein said switch is configured to selectively turn on one or both of said main and auxiliary lamps.

2. The laryngoscope handle according to claim 1, further comprising a magnifying glass disposed behind said area and rotationally articulated to one of said grip and said functional portion.

3. The laryngoscope handle according to claim 1, wherein said blade-retention portion comprises a securing arrangement configured to retain therein said blade.

4. The laryngoscope handle according to claim 1, wherein said slot is open to a surface of said blade-retention portion and wherein said slot comprises a primary channel spaced from said surface, and a secondary channel spanning between said primary channel and said surface.

5. The laryngoscope handle according to claim 4, wherein said primary channel projects outwardly from said secondary channel.

6. The laryngoscope handle according to claim 1, further comprising an arm connecting between said blade-retention portion said light source.

7. The laryngoscope handle according to claim 1, wherein said light source comprises a light emitting diode constituting a lamp thereof.

8. The laryngoscope handle according to claim 1, wherein said light source comprises a distal lens.

9. The laryngoscope handle according to claim 8, wherein said lens is configured to focus light from the light source to an angle between about 15° and about 20° along said viewing axis.

10. The laryngoscope handle according to claim 1, wherein said grip is formed with an internal battery compartment configured to electrically connect one or more batteries inserted therein to said light source to provide power thereto.

11. The laryngoscope handle according to claim 1, wherein said grip comprises a compartment for a coin cell battery.

12. The laryngoscope handle according to claim 11, wherein said compartment for a coin cell battery is formed within a removable cap of said grip.

13. The laryngoscope handle according to claim 1, wherein the area above said slot and to one side of said light source is substantially free of visual obstructions along said viewing axis.

14. The laryngoscope handle according to claim 1, wherein the area above said slot and surrounding said light source is substantially free of visual obstructions along said viewing axis.

15. The laryngoscope handle according to claim 1, being configured to receive a camera along said viewing axis.

16. The laryngoscope handle according to claim 1, being configured to receive a camera rotationally articulated thereto.

17. The laryngoscope handle according to claim 1, further comprising a transparent blade configured to be received within said slot such that when received within said slot, a proximal side thereof is positioned substantially in front of and facing said light source.

\* \* \* \* \*